United States Patent [19]

Arluck

[11] 4,169,469
[45] Oct. 2, 1979

[54] ORTHOPEDIC DEVICE

[75] Inventor: Elmer M. Arluck, New York, N.Y.

[73] Assignee: Yardney Company, New York, N.Y.

[21] Appl. No.: 868,338

[22] Filed: Jan. 10, 1978

Related U.S. Application Data

[60] Division of Ser. No. 758,786, Jan. 12, 1977, which is a continuation of Ser. No. 600,082, Jul. 29, 1975, Pat. No. 4,000,741.

[51] Int. Cl.² ............................................. A61F 5/04
[52] U.S. Cl. .................................................... 128/90
[58] Field of Search ................ 128/87 R, 89 R, 90, 128/156; 161/88, 89, 227, 257; 106/15 FP, 18; 260/2.5 AJ

[56] References Cited

U.S. PATENT DOCUMENTS

| 2,609,910 | 8/1952 | Herzfeld et al. | 260/342.4 |
| 3,278,580 | 10/1966 | Worsley et al. | 260/468 |
| 3,391,092 | 7/1968 | Worsley et al. | 260/2.5 |
| 3,403,036 | 9/1968 | Hindersinn et al. | 106/18 |
| 3,420,231 | 1/1969 | Edenbaum | 128/90 |
| 3,490,444 | 1/1970 | Larson | 128/90 |
| 3,929,700 | 12/1975 | Tybus et al. | 260/23 XA |

FOREIGN PATENT DOCUMENTS 1305834 8/1969 United Kingdom ................ 260/23

OTHER PUBLICATIONS

Ind. Eng. Prod. Res. Develop., vol. 11, No. 4, 1972, pp. 383–389.
Journal of Cellular Plastics, Jul./Aug. 1972, pp. 214–217.
Journal of Cellular Plastics, May/Jun. 1972, pp. 134–142.
Journal of Cellular Plastics, Sep./Oct. 1971, pp. 256–263.
Journal of Cellular Plastics, Nov./Dec. 1970, pp. 262–266.
Journal of Cellular Plastics, Jan. 1969, 46–50.

Primary Examiner—John D. Yasko
Attorney, Agent, or Firm—Karl F. Ross

[57] ABSTRACT

An orthopedic device comprising a plastic sheet member having one side covered with a thin protective layer which is substantially thinner than said plastic sheet member and the other side covered with an insulating layer, e.g., fabric or foam. The plastic sheet member has a tensile strength of at least 2,000 psi. The orthopedic device is formable at temperatures above about 120° F.

6 Claims, 5 Drawing Figures

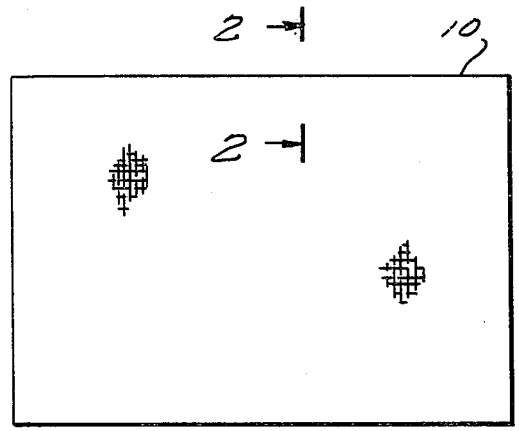
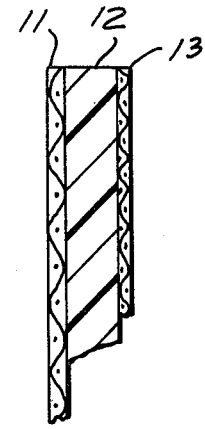
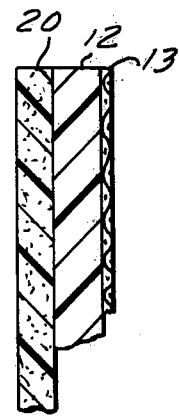
FIG. 1  FIG. 2a  FIG. 2b
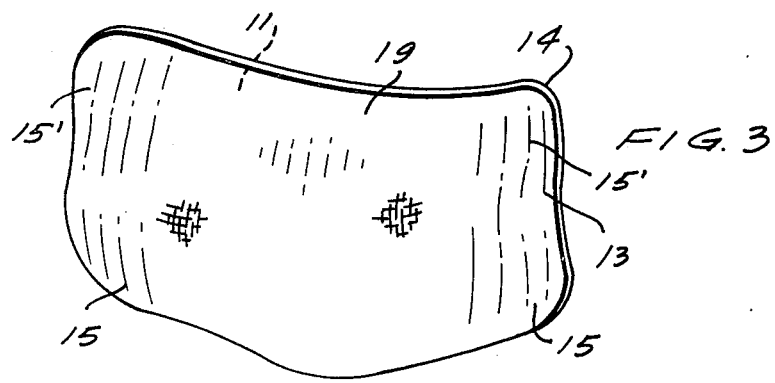
FIG. 3
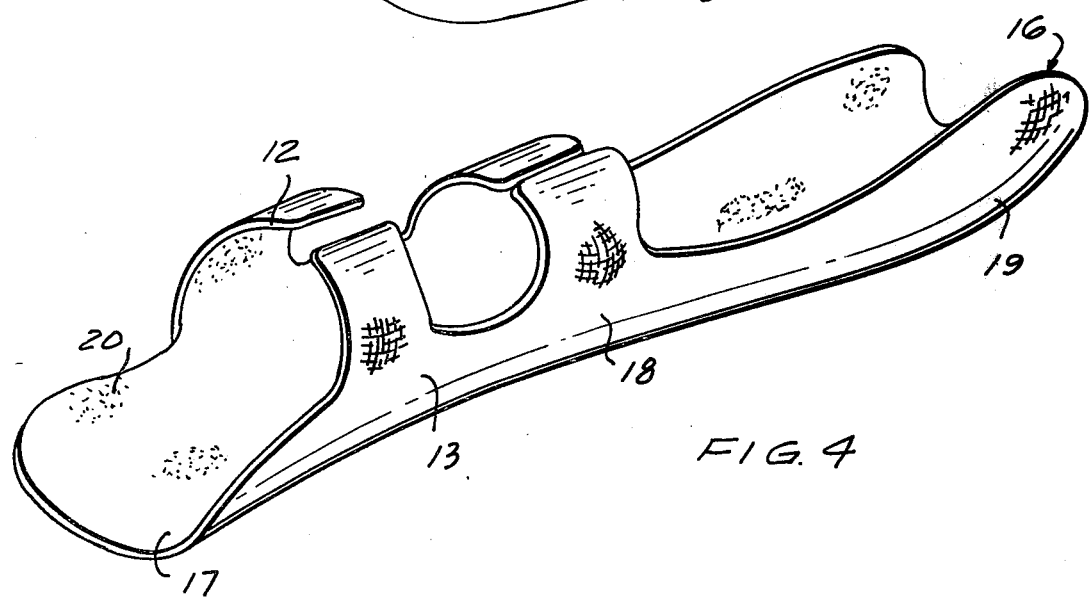
FIG. 4

ORTHOPEDIC DEVICE

This is a division of application Ser. No. 758,786, filed Jan. 12, 1977; which is a continuation of Ser. No. 600,082, July 29, 1975 U.S. Pat. No. 4,000,741.

BACKGROUND OF THE INVENTION

This invention relates to orthopedic devices having broad medical applications. These devices are used to support, position, protect, immobilize and/or restrain portions of the body.

Orthopedic devices are medical structures such as casts, splints, supports, braces and other means utilized to support, immobilize, restrain, protect and position body portions. They are used in many fields, including the physical medicine and rehabilitation field, general medicine, neurological field, and the veterinary field. They are also used to prevent recurrance of previous disabilities, and to prevent discomfiture and subsequent disability.

Different types of the known orthopedic devices have specific uses and it has been necessary to select a specific type of orthopedic device to meet the requirements of a specific intended usage. The treatment of fractures usually requires total immobilization. Casts made of Plaster or Paris (plaster) are commonly used for this purpose. Plaster casts have the disadvantage that plastic takes hours to harden, the cast is excessively heavy, has poor compression strength and is readily crushed or broken, and the material has poor resistance to water and poor x-ray penetrability. Splints have been made of wood and metal and even plastic. Those synthetic base orthopedic devices which have been proposed and/or introduced commercially by others have had disadvantages inherent in some or all uses.

Orthopedic devices should desirably be lightweight. They should be capable of immobilizing a portion of the body when that is the intended purpose. Similarly, they should be capable of resilient support and/or cushioning when that is required. The orthopedic device should be capable of being formed in a practical manner and without discomfort to the patient. Additionally, the orthopedic device should not have properties which irritate the patient during the period in which it is in service. Orthopedic devices fulfilling these requirements are disclosed in my copending application, Ser. No. 465,404, filed Apr. 29, 1974, now U.S. Pat. No. 3,906,943.

OBJECT OF THE INVENTION

It is an object of this invention to provide orthopedic devices having wide applicability and a unique combination of desirable properties.

SUBJECT MATTER OF THE INVENTION

The orthopedic device of the present invention is a plastic sheet member having at least one side covered with a thermally insulating layer. The plastic sheet member is at least about 40 mils thick. The insulating layer is at least about 10 mils thick. It is capable of being molded (formed) with application of normal finger pressure when the plastic is at a temperature above about 120° F. When the device is heated to substantially above its molding temperature, e.g., 165°–350° F., and allowed to cool in air and ultimately on the patient as it is being formed, the temperature at the outside of the insulating layer is at least about 25° F. cooler than the plastic member and preferably at least 40° F. cooler.

The orthopedic device has both sides of the plastic sheet member covered. The side covered with the insulating layer is the inside surface of the device and is the side intended to be placed against the body surface during service. The other side (the outside of the device) is covered with a fabric layer (referred to herein as the "outside" or "other" or "protective" which is preferably fabric and protects the plastic. The insulating layer is bonded to the plastic and the outside fabric layer is bonded to the plastic sheet member. The outside fabric layer is preferably between about 4 and 22 mils thick.

BRIEF DESCRIPTION OF THE DRAWING

FIG. 1 is a rectangular blank having a construction in accordance with the present invention.

FIG. 2a is an enlarged cross section along the line 2—2 of FIG. 1 of one embodiment of the invention.

FIG. 2b is an enlarged cross section along the line 2—2 of FIG. 1 of another embodiment of the invention.

FIG. 3 is a perspective of a formed back support having a construction in accordance with the embodiment of FIG. 2a; and FIG. 4 is a perspective of a formed arm splint having a construction in accordance with the embodiment of FIG. 2a.

SPECIFICATION DESCRIPTION

When the insulating layer is a fabric, it may be a woven, felted, matted, batted or knitted fabric. When it is a woven fabric, it is preferably between about 10 mils and 22 mils thick. Some fabrics, e.g., felt, may be considerably thicker and provide cushioning. The preferred insulating fabric is a woven blend, preferably 50:50, of a high-temperature aromatic polyamide, now generically classified as an aramid, and a high-temperature cross-linked phenol-formaldehyde fiber, such as the no-burn fabrics marketed by Collins & Aikman Corp. which are blends of 50% Kynol and 50% Nomex. Nomex is a trademarked porduct of the Du Pont Company and is the high-temperature aromatic polyamide. Kynol is a trademarked product of the Carborundum Company and is a cross-linked phenol-formaldehyde fiber, such as that described in U.S. Pat. No. 3,650,102. An aramid fabric may also be used.

The insulated fabrics may be used in weights of about 4 oz. per square yard, up to about 16 oz. per square yard. The preferred weight is about 5 to 8 oz. per square yard.

The insulating layer preferably should have a coefficient of heat transfer below about $2$ cal/sec/cm$^2$/cm/°C$\times 10^{-4}$, and more preferably below about $1.6$ cal/sec/cm$^2$/cm/°C$\times 10^{-4}$.

When the insulating layer is a fabric layer, it is preferably affixed to the central plastic member with an adhesive, preferably a thermoplastic adhesive. Since relatively high shaping and molding temperatures, e.g., 400° F., may be used to shape the orthopedic device, the thermoplastic adhesive should be one which will remain bonded to the fabric and to the central plastic member at the temperatures used to heat and form the device. It is preferred that it should retain said property at temperatures above 200° F. and, for an added safety factor, it is preferred that it should retain said property at above about 350° F. for devices which will be shaped before service.

The outside adhesive may be a polyurethane, preferably a flexible thermoplastic polyester type polyurethane adhesive. This material also has the advantages of good resistance to perspiration, washing and dry cleaning. Although the polyester type polyurethanes are preferred, polyether types may also be used. Thermosetting polyurethane adhesives may also be used, such as hydroxyl terminated hexanediol adipate polyester cross-linked with about 4% of 4,4'-diphenyl methane diisocyanate, which is preferably halogenated to improve its flame retardancy.

An extruded polyester sheet about 2½ to 3 mils thick is also a preferred adhesive. It is positioned between the central plastic sheet and the fabric layer and the materials heated to about 350° F. at a pressure of 1 to 2 psi to affix the fabric to the central plastic member.

Alternative but less preferred adhesives include the acrylates, such as polyethyl acrylate, polybutyl acrylate, and polyethylhexyl acrylate; and a polyvinyl acetate homopolymer and a copolymer of ethylene and vinyl acetate. The adhesive may also be blends of the foregoing.

The adhesive may be coated as a thin layer on the central plastic member and the fabric layer positioned on the adhesive, usually with the application of pressure. This will usually result in the adhesive penetrating into the fabric layer. With a combination of a sufficiently thin adhesive layer and sufficient pressure during application, there may be some direct contact of some of the fabric with the central plastic member.

The fabric, particularly when woven, may be partially or wholly impregnated with a plastic adhesive before being applied to the central plastic layer. The preferred insulating fabric layers are partially impregnated, with the impregnating plastic being applied from one surface to a depth of between about 0.1 mil and 7 mils and preferably between about 0.05 and 5 mils. This results in a thin coating on the surface of the fabric, which is applied hot (or heated after application) and affixes the impregnated fabric to the central plastic member.

The fabric layer may also be bonded to the plastic member by fusing, i.e., heating until the plastic is viscous, at a temperature above about 325° F., and then contacting the fabric with pressure so that the surface of the plastic partially impregnates the fabric and upon cooling is bonded thereto.

The insulating layer may also be a plastic foam layer. The foam layer provides sufficient insulation so that the outer surface of the foam layer may contact the person without severe discomfort while the plastic sheet member is still soft and usually at a temperature substantially in excess of about 120°–130° F. The insulating foam layer may also function to cushion the portion of the person against which the orthopedic device is applied.

Since foam layers may be produced having substantially differing insulating characteristics and since the amount of padding desired varies in different applications, the thickness of the foam layer may vary from as little as about 10 mils up to about 300 mils. For most service applications in which some cushioning is desired and/or is not detrimental, foam layers having a thickness of between about 125–250 mils are preferred. Even thicker layers, e.g., up to about 500 mils, may be useful to pad a portion of an orthopedic device which will contact a boney portion of the person, particularly when pressure may be applied by this boney portion against the orthopedic device. In some applications in which very precise positioning of the body portion without the possibility of movement is desired, relatively thin foam layers, e.g. with a thickness between about 25 and 75 mils, are useful. In some applications, a thin foam layer may be used largely because there is no further advantage to a thicker layer and the thin layer would be more economic.

It is preferred that the foam layer should be relatively stiff so that it does not readily compress under pressure. This has the advantage that the insulating characteristic of the foam is retained when the foam layer is under pressure. This is particularly important since the orthopedic device is usually "pressed" against the body when it is formed. A relatively stiff foam layer is also an advantage in that it provides more accurate positioning and minimizes the amount of permissible movement of the body portion against which the orthopedic device is applied. The foam layer comprises a cellular structure having a great many pores in the plastic material. The foam may be of a closed pore construction or of an interconnected (open) pore construction, or a combination of both as is the usual instance. The relative stiffness of the foam is preferably controlled by the selection of polymer constituents which produce a relatively stiff foam.

When the orthopedic device is heated sufficiently so that it will remain soft for several minutes during which it is shaped and formed, the plastic sheet member is usually heated to a temperature well above 200° F. and is often heated to temperatures of at least 300° F. and sometimes up to as much as about 350°–375° F. The insulating foam layer must remain stable at the temperature to which the orthopedic device is heated. If the foam layer is not stable at these temperatures, the cellular structure would collapse as a consequence of viscous flow, particularly when pressure is applied. Since destruction of the cellular structure would impair the insulating characteristics of the foam and also the cushioning characteristics of the foam, those foams which are stable at above 200° F. are preferred and those foams which are stable at temperatures as high as at least 300° F. are particularly preferred.

It is preferred that the foam layer should not support combustion, i.e., not burn, and that it should have at least as good flame-retardant characteristics as the plastic sheet member which is preferably a polyvinyl chloride composition. It is preferred that the foam layer should not support a flame in the absence of an external flame.

The preferred materials for use as the foamed layer are those which are (i) fire-retardant and (ii) stable at temperatures up to about 200° F., and preferably up to about 325° F. The foam materials that meet these characteristics are thermosetting materials, or if they are thermoplastic, very high temperature thermoplastics. The foam should also be sufficiently flexile so that it may be bent during forming, and is preferably resistant to perspiration and washing, and even dry cleaning.

The following are the preferred materials for forming the foam layer:

(1) Polyolefin foams such as prepared from polyethylene, cross-linked polyethylene and polypropylene. Characteristics of polyethylene foams are disclosed in the Journal of Cellular Plastics, January, 1969, at pages 46–50, which disclosure is incorporated herein by reference. Particularly preferred are fire retardant polyolefin foams, such as fire retardant polyethylene. A useful method for fire retarding polyethylene and other polyolefins is to incorporate into the polymer fire retardant additives such as the Diels-Alder adducts of a hexahalocyclopentadiene, such as hexachlorocyclopentadiene. Particularly useful adducts for this purpose are disclosed in U.S. Pat. No. 3,403,036 and British Pat. No. 1,305,834, the disclosures of which are incorporated herein by reference. A metallic additive such as antimony trioxide is also desirably incorporated in the polymer together with the disclosed adducts.

(2) Polyurethane foams such as those prepared from polyether polyols or polyester polyols and mixtures thereof. The polyether urethanes are preferred and especially preferred as the fire retardant polyether urethanes. The polyether urethanes can be rendered fire retardant by the incorporation of non-reactive additives, usually phosphorus-containing or halogenated compounds, but fire-retardant concentrations are held at low levels to prevent degradation of foam properties. A typical non-reactive additive is a chlorinated phosphorus-containing ester produced by Monsanto Chemical Company under the tradename Phosgard 2XC-20. Reactive compounds can also be included in the polyether urethanes to provide fire retardance. This method is disclosed in U.S. Pat. Nos. 3,278,580 and 3,391,092, the disclosures of which are incorporated herein by reference. The latter method involves utilization of chlorendic acid as the basic component in the formation of the polyether polyol. Another approach is a system of post-treating flexible foams with fire retardants. The system involves soaking the finished foam in aqueous suspensions of inorganic flame retardants such as magnesium ammonium phosphate and water-soluble binders that are water resistant after drying. After the foam has dried, the flame-retardant characteristic is permanent and there is no loss of foam properties. Another approach to fire retarding the polyether urethane foams involves the production of "high resilience" foams such as disclosed in Journal of Cellular Plastics, July/August, 1972, at pages 214-217, the disclosure of which is incorporated herein by reference. Additional useful fire retardant urethane foams utilizing additives such as tris(dibromopropyl) phosphate and tris(dichloropropyl) phosphate, are disclosed in Journal of Cellular Plastics, November/December, 1970 at pages 262-266 and Journal of Cellular Plastics, May/June, 1972 at pages 134-142, both of which are incorporated herein by reference. Fire retarded polyester-urethane foams are also useful such as those disclosed together with additional polyether urethane foams in Ind. Eng. Chem. Prod. Res. Develop., Volume 11, No. 4, 1972 at pages 383-389, the disclosure of which is incorporated herein by reference. Additional fire retardant urethane foams are disclosed in the Journal of Cellular Plastics, September/October, 1971, at pages 256-263, the disclosure of which is incorporated herein by reference.

(3) Fire retardant ABS foams (acrylonitrile-butadienestyrene) are prepared in fire retardant form by preparing the ABS compositions, for example, composed of 30% acrylonitrile, 35% butadiene, and 35% styrene, as is well known in the art. The fire retardant materials and processes for incorporating them into the ABS compositions are essentially the same materials and processes as those described hereinbefore for incorporation into polyolefin foams.

(4) Fire retardant polyester foams are also suitable. Polyester foams generally are formed by reacting a polyol, generally a polyester polyol or polyether polyol with a polycarboxylic (preferably a dicarboxylic) acid such as adipic acid or sebacic acid. Typical polyols include butanediol and polytetramethylene ether glycol. Fire retardant properties may be incorporated into the polyester by preparing the polyester and then soaking the finished foam in aqueous suspensions of inorganic flame retardants as described hereinbefore in connection with the polyurethane foams. The fire retardant properties also may be built into the foam by incorporating chlorendic acid as a partial or total replacement for the carboxylic acid, as disclosed in U.S. Pat. No. 2,606,910 which is incorporated herein by reference. The polyester foams are generally foamed by admixing a blowing agent utilizing similar technology to that used in forming polyolefin foams.

(5) Although polyvinyl chloride foams generally are not stable at temperatures above 160° F., a polyvinyl chloride composition alloyed with an acrylonitrile-butadiene-styrene terpolymer may be used in applications wherein stability above about 200° F. is not required. Post-chlorinated polyvinyl chloride foams are stable at elevated temperatures. These are highly stabilized thermoplastic materials and form stable foams.

(6) Suitable foams may also be formed from fluorocarbon elastomers which at present are very expensive.

(7) Additional foamed plastics include acrylic, cellulose acetate and epoxy foams, such as disclosed in 1974-1975 Modern Plastics Encyclopedia at page 720, the disclosure of which is incorporated herein by reference.

The foam layers are formed using the foam producing production methods which are well known in the foam material technology, e.g., Modern Plastics Encyclopedia, 1974-1975, Vol. 51, No. 10A, (Oct. 1974) pages 125-155 the disclosure of which is incorporated herein by reference. The precise foam constituents and production technique varies somewhat dependent upon the specific polymer(s) which forms the basic foam material. Thus, the polyurethanes may be foamed in the presence of small amounts of water which react with the isocyanate to produce carbon dioxide, without requiring additional foaming agents. In some instances foaming gases or gas-producing materials are used. Mechanical frothing may also be used in the production of certain foams, e.g., polyurethanes and polyesters. The polymer is dispersed in water, e.g., 40-65% by weight of solids and mechanically mixed by a high shear mixer to incorporate air and is then cast on sheet material and dried by heating to remove water.

The foam layer may be produced directly on the plastic sheet member or on a fabric layer using the direct coating process. The transfer coating process also may be used in which the foam material is knife coated on release paper (generally silicone treated paper) and then transferred to a fabric or the plastic sheet member or even a metal substrate and cured. In the usual instance it is contemplated that the foam layer will be formed on a fabric or a inert high temperature substrate such as a polished metal, and cured. If a fabric is used, it should be a high temperature stable fabric, such as the high temperature stabilized polyesters and/or nylons. High temperature stabilized polypropylene such as a needle punch polypropylene fabric about 8-10 mils thick is also suitable. Although a fabric may be used, it is not necessary in order to produce a pleasing and even a decorative effect. These may be produced directly on the surface of the foam using printing or embossing rolls.

The foam layer may be fixed to the plastic sheet member by conventional methods such as the use of adhesives, application of pressure, flame bonding, etc. The bonding method selected depends upon the composition of the plastic sheet member and the composition of the foam layer. When the plastic sheet member is a polyvinyl chloride composition, and the foam layer is a polyolefin foam or an ABS foam, the preferred method of bonding utilizes ethylenevinylacetate copolymer as an adhesive to form the bond. Polyether polyurethane foams and polyester foams are also preferably bonded to polyvinyl chloride sheet composition using an adhesive, preferably a thermosetting polyurethane such as a hydroxyl terminated hexanediol adapate polyester cross-linked with about four percent of 4,4'-diphenol methane dioscyanate. The said thermosetting polyester urethane adhesive is preferably halogenated to further the flame-retardant characteristics of the orthopedic device. The said thermosetting polyurethane adhesive is also useful for bonding polyvinyl chloride foams to polyvinyl chloride sheet material.

Polyester polyurethane foams are preferably flame bonded to polyvinyl chloride sheet material.

Foam layers, preferably those having a coarse interconnected cellular structure (at least at and near the skin) may be fixed to a thermoplastic sheet member by heating the thermoplastic sheet member until it has softened and contacting the sheet member and the foam layer under pressure, e.g., by passing the heated thermoplastic sheet member and the foam layer through rolls.

The strength and flexural properties of the orthopedic device at ambient temperatures are largely contributed by the plastic central member. This member is strong and has the ability to be resilient in some configurations and sizes. It has the ability to be substantially rigid in specific configurations, i.e., O-sections, L-sections, U-sections, etc. A device may include several different configurations and be substantially rigid in a specific area and quite resilient in another area thereof.

The versatility of the orthopedic devices is illustrated by the following properties of the plastic sheet. Different configurations were prepared from sheet (90–93 mils thick) having the composition illustrated hereinafter. The sheet was 6⅜ inches long.

An "O" configuration was prepared with a radius of tube 13/16 inches. The tube was held with clamps at each end. It was supported on two focal points 4 inches apart at the bottom, and the load applied from the top to the center of the tube. The deflection follows:

| Machine Deflection[a] in Inches | Load in Pounds |
| --- | --- |
| 0.1 | 49.5 |
| 0.2 | 51.2 |
| 0.3 | 80.5 |
| 0.4 | 104.0 |
| 0.5 | 125.0 |
| 0.6 | 142.0 |

(a) The machine deflection includes bending of the tube over its entire length, and flattening of the tube at all three focal points.

A "U" configuration was prepared with a 2⅜ inches width of configuration and a 29/32 inch radius of bend. The arms of the "U" were mounted parallel to the horizontal (held in vice) and the load applied to the upper arm. A constant load test provided the following:

| Points at which Constant Load (1 lb.) was Applied, Measured in Inches from Center of "U" | Deflection in Inches at Constant Load (logarithm) |
| --- | --- |
| 1.15 | 0.050 |
| 1.75 | 0.095 |
| 2.75 | 0.135 |
| 3.75 | 0.175 |
| 4.75 | 1.145 |

A constant deflection test provided the following data:

| Points at which Constant Deflection (0.45 inches) was obtained, Measured in Inches from Center of "U" | Load in pounds at Constant Deflection (logarithm) |
| --- | --- |
| 4.75 | 0.30 |
| 3.75 | 0.60 |
| 2.75 | 1.18 |
| 1.75 | 8.60 |
| 1.15 | 10.73 |

Two "L" shaped configurations were prepared by holding in a vice vertically and bending to form a right angle. The load was applied vertically and placed on horizontal arm.

The results of a constant load test on a sample having a 2 7/16 inches width of configuration and ¼ inch radius follows:

| Points at which Constant Load (2 lbs.) was Applied, Measured in Inches from Center of Bend | Deflection in Inches at Constant Load (logarithm) |
| --- | --- |
| 0.5 | 0.010 |
| 1.0 | 0.025 |
| 1.5 | 0.070 |
| 2.5 | 0.280 |
| 3.5 | 0.680 |
| 4.5 | 1.150 |

The results of a constant deflection test on a sample having a 2⅜ inches width of configuration and a 29/32 inch radius follows:

| Points of which Constant Deflection (0.35 inches) was obtained, Measured in Inches from Center of Bend | Load in Pounds at Constant Deflection (logarithm) |
| --- | --- |
| 4.5 | 0.50 |
| 3.5 | 1.00 |
| 2.5 | 2.27 |
| 1.5 | 12.00 |
| 1.0 | 40.00 |

The physical properties of the plastics vary somewhat with the thickness of section tested. Specific physical properties such rigidity and/or resilience of the orthopedic support vary with the thickness and overall size dimensions of the plastic central layer. The central plastic layer is usually between about 50 mils and about 120 mils, although thicker layers, e.g., up to about 250 mils thick, may be utilized for large sections, such as a major body cast, e.g., about 200 mils thick, where substantial rigidity is required to support a large weight. Thick sections, e.g., about 150–170 mils, would also be used to provide orthopedic devices used to precisely position the body portion for radiation therapy. Devices (in blank form, i.e., flat) used for preparing back supports, are preferably about 65-80 mils thick. Blanks for splints and braces are preferably about 80-120 mils thick. The preferred blanks for highly shaped casts may be of a variety of widths dependent upon the final configuration and service requirements. When thin devices, e.g., 40-50 mils of plastic central member, are used, additional strips or pieces of plastic sheet may be fixed to the outside surface to reinforce the device.

The plastic preferably has a tensile strength (at yield) of between 2,000 and 10,000 psi and more preferably between 5,000 and 8,000 psi (ASTM D-638). The central plastic layer is relatively stiff as reflected by a percent elongation at yield of between about 3 and 30% and preferably between about 4 and 8%. The properties to yield are more important than to rupture since the properties should not exceed yield in service.

The flexural strength (ASTM-790) is between 3,000 and 14,000 psi and preferably between 8,000 and 12,000 psi. The flexural modulus (ASTM-790) is between $0.5 \times 10^5$ and $7 \times 10^5$ psi and preferably between $2 \times 10^5$ and $5 \times 10^5$ psi. The notched Izod (ASTM D-256) in foot-pounds per inch is between 0.3 and 30 and preferably between 0.5 and 15.

The Rockwell hardness is between 15 R scale and 55 D scale and preferably between 90 and 100 R scale. The Vicat softening point (ASTM D-1525-70) is between 60° C. and 80° C.

A sample of the preferred impact modified polyvinyl chloride plastic member which is illustrated in the Example has an average tensile ($\pm 100$ psi) at yield of about 7,550 psi and at rupture of about 3,800 psi (ASTM D-638). The average ($\pm 0.5\%$ percent elongation at yield is 5% and the average percent elongation at rupture is 14.2%. The average flexural strength is $10.8 \times 10^3$ psi and the flexural modulus is $4.1 \times 10^5$ psi (ASTM d-790).

Another sample of the same composition had a tensile strength at yield of 6.785 psi; an elongation at yield of 5.6%; a flexural modulus of $3.94 \times 10^5$ psi; a flexural strength of 11.612 psi; a Rockwell R hardness of 94; a Vicat of 74° C.; and a notched Izod of 0.91 foot pounds per inch.

Another sample of the same composition which had been severely worked during processing, but found operative had a tensile strength at yield of 3.620 psi; an elongation at yield of 4.5%; a flexural modulus of $1.06 \times 10^5$; a flexural strength of 3.724 psi; a Rockwell R of 19; a Vicat of 63° C.; and a notched Izod of 12.5 foot pounds per inch.

The central plastic member may be formulated from various polymer systems, such as vinyl-chloride-propylene copolymers, vinyl-chloride-ethylene copolymers, or the corresponding interpolymer containing diallyl maleate. It is preferred to utilize an impact modified polyvinyl chloride (PVC) composition utilizing a PVC resin having a number averaging molecular weight of 20,000-23,000. The composition contains between about 10 and 14 parts of an impact modifier, between 1¼ and 2 parts of lubricant, and between 7½ and 8½ parts of a plasticizer, per 100 parts of polyvinyl chloride homopolymer resin. The composition will also contain stabilizers (6+9) parts and various processing aids (1.5 to 2.1 parts) and usually pigments (up to 5 parts).

A preferred PVC composition and exemplified composition follow:

| COMPONENTS | Preferred Range (parts) | Preferred Composition (parts) |
|---|---|---|
| PVC homopolymer resin (20,000-23,000) | 100 | 100 |
| impact modifier (methylmethacrylate-butadiene-styrene polymer | 10-14 | 12.0 |
| processing aid (acrylic type)* | 1.5-2.1 | 1.8 |
| lubricant | | |
| blend of olefinic monoglyceride and hydrogenated olein | 1-1.5 | 1.25 |
| tri-stearyl citrate | 0.25-0.35 | 0.3 |
| plasticizer (di-2-ethylhexyl phthalate) | 7.5-8.5 | 8.0 |
| stabilizer boosters | | |
| epoxidized soybean oil | 4-6 | 5.0 |
| mixed di- and tri-nonylphenyl phosphite | 1.25-1.75 | 1.5 |
| polyvinyl alcohol | 0.05-0.08 | 0.0675 |
| stabilizers | | |
| calcium stearate | 0.24-0.30 | 0.27 |
| stannous stearate | 0.37-0.43 | 0.40 |
| zinc stearate | 0.28-0.34 | 0.31 |
| pigments | 2.5-3.5 | |
| rutile grade TiO$_2$ | | 3.25 |
| Hosterperm Red | | 0.0054 |
| Indofast Orange | | 0.0135 |

*Rohm & Haas K-120 N

A sheet of the polyvinyl chloride having a thickness of about 80-90 mils was prepared from small pellets about ⅛"×3/16" in diameter. The pellets were heated in an extruder and the resin composition extruded in the form of a rope-shaped material of a diameter of about ½" which is then milled in rollers and calendered into sheet about 15-20 mils thick. Four sections of such sheet were laminated together in a press with a heated die to form sheets about 80-90 mils thick. The physical properties of this test sheet were reported hereinbefore. Additional details concerning the said plastic compositions and the manner of producing them are disclosed in copending application, Ser. No. 465,403, filed Apr. 29, 1974 entitled "POLYVINYL CHLORIDE COMPOSITION" and naming AXEL W. TYBUS and LEONARD A. FABRIZIO as the inventors. The disclosure of said copending application is incorporated herein by reference.

The polyvinyl chloride sheet material may be formed in production by heating the small PVC composition pellets in an extruder and directly extruding in sheet form having the desired thickness. An alternate procedure is to mill and calender rope-shape material of a diameter from about ½" to 4". Sheet material taken from such processes and particularly direct extrusion is stressed and is preferably stress relieved by annealing at temperatures of about 320° F. It is possible to anneal simultaneously with the application of an adhesive or an adhesive and fabric.

The outside layer which is preferably fabric (but could also be another material such as a metallic layer) protects the plastic surface from damage during shipment, storage and handling of the flat orthopedic device before it is molded and also to protect it after it has been shaped. If a heating element is used, for example, a hot iron, directly in contact with the orthopedic device, the outside fabric layer serves to prevent adherence of the plastic to the heating element.

This outside layer also functions together with the insulating fabric layer to maintain the coherency of the orthopedic device when it is heated to elevated temperatures. Since the outside fabric layer is bonded to the plastic, it will be in tension when the orthopedic device is shaped into a curve with the outer fabric layer on the outside of the curve. It is, therefore preferably of a resiliant or stretch material which will not apply pressure on and tend to distort the plastic layer at ambient and particularly at elevated shaping and/or forming temperatures.

During heating, the outside fabric layer may be subjected to very high temperatures. The preferred fabrics are those resistant to prolonged heating at 250° F. and short term heating to substantially higher temperatures. These high temperature resistant fabrics include the high temperature stabilized nylons; the high temperature stabilized polyesters; the Spandexs (polyurethanes); the aramids; such as Nomex; high temperature acrylics; the aforedescribed Collins & Aikman blends of 50% Kynol and 50% Nomex and particularly the lighter weight fabrics; and linen. The said nylons, polyesters, and aramids, are preferred.

For devices which are not to be heated to elevated temperatures, i.e., they are available in blanks generally conforming to the desired end shape, and which are only heated for forming, lower temperature fabrics, such as cotton and wool may be used.

The outside fabric layer is at least about 4 mils thick, and preferably between about 4 and 22 mils thick and most preferably between about 10 and 15 mils thick. It is preferably affixed to the plastic central member by an adhesive such as a thermoplastic polyurethane resin. Even thinner outside layers may be used, e.g., only 1-2 mils of metal plated or laminated on the plastic sheet member. The protective layer need not cover the entire surface of the one side of the plastic sheet, e.g., portions of the plastic may be covered by reinforcing plastic sheet strips.

The outside fabric layer may be fixed to the central plastic layer. Orthopedic devices have been prepared by first affixing a insulating fabric layer to the central plastic member by passing a three-layered material comprising the central plastic member and extruded polyester film of about 2½-3 mil thickness and the 7 oz. Collins & Aikman fabric described hereinbefore through a Reliant roll press which was at 350° F. and applying 1 to 2 psi for 18 seconds. The extruded polyester film was a thermoplastic. The other fabric film, the 4 oz. Collins & Aikman fabric described hereinbefore, was then affixed to the other side of the central plastic member by passing the aforedescribed insulated fabric coated central plastic member together with said fabric and an interposed 2½ to 3 mil sheet of the polyester film through the Reliant roll press under the aforesaid conditions. It is preferred to produce the orthopedic device by passing the two outer layers and the central plastic member and the respective adhesive layers, which may be preapplied to the fabric or plastic foam, through the roll press simultaneously to produce the integral orthopedic device in a single pass. The blank orthopedic device may also be prepared by extruding the plastic sheet member onto a coated fabric or even coextruding the fabric layers and the plastic sheet together with the intervening adhesives.

At the shaping and forming temperatures the orthopedic device is readily cut. The cutting may be carried out by shears, for example, a scissors, or some other sharp edge. Those orthopedic devices having both sides of the plastic member covered by fabric layers retain integrity even at elevated temperatures. When it is desirable to carry out extensive shaping and forming of the orthopedic device such as forming a coil by wrapping various layers of the orthopedic device about each other in a spiral, the temperatures may be elevated, e.g., up to about 250°-400° F. At these temperatures the device maintains its integrity but becomes highly pliable. The orthopedic device may be cut and the plastic does not run out from between the outer layers. When the orthopedic device is heated to such high temperatures and removed from the source of heat, it may be shaped and molded and formed over a period up to about 6-10 minutes. The rough shaping is carried out as the orthopedic device begins to cool from this elevated temperature. When the outer surface of the insulating layer is cooled sufficiently, it may be pressed against the body portion to be formed into its final shape, generally under finger pressure. After the orthopedic device is applied against the body, there is still sufficient time during which final molding to conform to the desired body and/or device shape may be carried out.

The orthopedic device may be heated in a constant temperature fluid bath, such as a water bath or a hot oven or radiant energy. It is preferred that heat be applied only to the side of the orthopedic device which will not be applied against the patient. This may be accomplished by radiant heat, a hot air gun or hairdryer and preferably because of their ready availability, a hot plate or tray home iron or even a special round or curved iron. Surprisingly, it has been found that the hot surface of an iron, which may be at hot as 300°-500° F., may be applied to the fabric layer of the orthopedic device and heat it to temperatures at which it becomes extremely pliable so that it may be cut and shaped to extremely complex shapes. The heat source is removed and/or intermittently applied and the orthopedic device applied against the body portion and molded to the desired shape. The molding or forming may be carried out by finger pressure. The person applying and forming the orthopedic device may wear gloves. When a hot tray is used and the device covered by a protective dome, a temperature of 200° F. will over a period of time furnish sufficient heat so that the device will remain formable for the desired working time.

The upper temperature limit which may be applied against a portion of the human body varies dependent upon the area of skin in contact with the heat, the time of contact, and the individual tolerance to high temperature. For the purpose of applying orthopedic devices, the temperature should not be above about 120° to 125° F. for short term contact and preferably below 120° F. for contact of several minutes.

When the orthopedic device in blank form is pre-cut and requires only forming, it may be heated to a temperature between about 165°-225° F. from one side, and when the outside of the insulating fabric layer is sufficiently cool, applied to the patient's body and formed into the desired contoured shape.

The central plastic member of the orthopedic device exemplified herewith solidifies at a temperature of about 129°-130° F. As a consequence, it is necessary that the temperature of the plastic central member should be above about 130° F. during forming. Since application of this temperature to the patient's skin for more than a very short time is uncomfortable and possibly dangerous, the outer temperature of the insulating fabric layer should be at least 25° F. cooler than the temperature of the plastic central member during forming, and is preferably at least 30° F. cooler. It is even more preferred that the outer temperature be at least 35° F. or 40° F. cooler than the plastic. The foregoing particularly applies during the plastic forming range of 130° F. up to about 160° F. The temperature at which the plastic sheet members softens permitting the orthopedic device to be formed may be varied from about 120°–123° F., up to about 145°–155° F. by varying the composition of the polyvinyl composition comprising the central plastic sheet. The aforenoted temperature difference may be larger, e.g., at least 50° or 60° F. when the device softens at a higher minimum temperature, e.g., above about 145°–155° F. A foam insulating layer is particularly suitable.

In a preferred embodiment of the invention, the heat is applied against the side of the orthopedic device covered by the outside fabric layer. For some service conditions it is contemplated that both sides of the plastic central member may be covered by insulating material. This would permit the entire member to be heated to an elevated temperature and retain the heat for a longer period of time.

The molded orthopedic device may be in many forms dependent upon the intended service and particularly the portion of the body to which it is applied. The orthopedic device when manufactured will be in the form of sheet material. For most purposes, these sheet blanks will be in a variety of sizes such as squares from about 4 inches on a side up to about 2 feet on a side and even larger sizes, e.g. 2'×4' or more. Rectangular and even oval or round blanks may be prepared. These blanks will have the central plastic member in sheet form with the insulating layer bonded on one side and the other layer bonded on the other side. Such blanks may have a total overall thickness somewhat less than the sum of the thickness of the plastic central member plus the two outer layers as a result of the manufacturing.

The invention is further illustrated by the following Example and drawings:

FIG. 1 of the drawing illustrates a rectangular-shaped blank (flat orthopedic device) 10 having a protective FIGS. 2a and 2b illustrate two embodiments of the invention along line 2—2 of FIG. 1.

FIG. 2a illustrates a preferred embodiment of the invention in which the insulating layer 11 is on one side of the plastic sheet 12 and the other side of the plastic sheet 12 is covered by the protective fabric layer 13. The relative thickness of the layers in all the drawings is for illustrative purposes only.

FIG. 2b depicts a preferred embodiment of the invention in which one side of the plastic sheet 12 is covered by the protective layer 13 and the other side is covered by the insulating layer 20.

FIG. 3 illustrates a shaped and formed back support 14 with formed contours such as those illustrated at 15 and 15'. The central portion 19 is relatively fixed and supports the spinal area and portions 15 and 15' are more resilient and support the back and related lower body portions.

FIG. 4 illustrates an arm splint 16 having hand section 17, wrist section 18, and forearm section 19, with the insulating foam layer 20 (not depicted in the edges) on the inside surface and a protective layer 13 on the outside surface.

The invention is further illustrated in the following Examples. All parts and percentages are by weight unless specified otherwise.

EXAMPLE 1

A flat blank orthopedic device was formed from a plastic sheet member of a thickness of 91–93 mils and having the composition set forth in the righthand column of the table hereinbefore was coated on one side with the woven insulating fabric which is the non-burning blend of 50% Kynol and 50% Nomex described hereinbefore. This insulating fabric had a weight of about 7 ounces per square yard and was about 14 mils thick. It was impregnated from one side with a polyester flexible polyurethane thermoplastic adhesive to a depth of about 3 mils on one side. A thin coating remained on the side to which the impregnant was applied. It was bonded to the plastic member by heating the impregnated insulating fabric to a temperature of about 325° F. and then covering the plastic sheet and applying light pressure. The other side of the plastic sheet was covered by a knit stabilized nylon fabric of a thickness of about 14 mils similarly impregnated with the same adhesive. It was similarly bonded to the plastic member.

EXAMPLE 2

One-hundred parts of a fine powder, e.g., 40–50 microns of a partially cross-linked polyethylene which will produce a generally stiff but flexible foam is mixed with 6–10 parts of titanium dioxide pigment and about four parts of bisazodicarbonamide, and mixed until homogeneous. It then was spread in a thin sheet on silicone coated paper and passed into an oven and heated to 170°–190° C. over a period of up to about ten minutes. The bisazodicarbonamide decomposes liberating nitrogen and causing formation of foam. The resultant foam layer is about 125 mils. Another thicker layer was formed to about 250 mils. The newly formed foam is then cooled quickly by passage through a cold water trough. The resultant foam was sufficiently flexible to be bent back up on itself. Its density is 4.1 pounds per cubic foot. The pores are predominantly of the closed type in the area of the skin.

Samples of sheet of the above foam about 125 mils thick, and also of 250 mils thick, are adhered to a sheet of said central plastic member formed from PVC with the thermosetting polyurethane adhesive described hereinbefore. The other side of the PVC was coated with the tricot as described in Example 1. The resultant device had desirable orthopedic device characteristics. The disadvantage was that the polyethylene was not fire retardant.

EXAMPLE 3

Example 2 is repeated using a fire retardant composition comprising 75 parts of polyethylene, 25 parts of Diels-Adler diadduct of hexachlorocyclopentadiene and 1,5-cyclooctadiene, 10 parts of antimony trioxide, 6–10 parts of titanium dioxide, and about 4 parts of bisazodicarbonamide. A third foam layer about 50 mils thick is used in place of the thicker layers of insulating foam in Example 2.

EXAMPLE 4

Example 2 is repeated substituting for the polyethylene foam of Example 1, a polyethylene foam having a density of 4.0 pounds per cubic foot, a thermal conductivity of 0.40 Btu/Sq. ft./hr. degrees F./inch as measured by ASTM D2326, a water vapor transmission as measured by ASTM C355 of <0.40 perm-inch and a water absorption of <p.50 percent by volume (96 hours) as measured by ASTM D2842.

EXAMPLE 5

Example 2 is repeated using a cross-linked polyethylene foam having a density of about 4 pounds per cubic foot, a thermal conductivity of 0.40 Btu/sq. ft./hr. degrees F./inch as measured by ASTM D2326, a water vapor transmission of <0.40 perm-inch as measured by ASTM C355 and a water a absorption of <0.50 percent by volume (96 hours) as measured by ASTM D2842.

EXAMPLE 6

Example 2 is repeated using a commercially available fire retardant polyurethane foam having an ASTM D1692-68 classification of SE (self-extinguishing) and a density of 4.18 pounds per cubic foot (67 kg/m$^3$). A foam layer about 25 mils thick is used in place of the thicker foam layer of Example 2.

EXAMPLE 7

Example 2 is repeated using a fire retardant composition comprising 60 parts by weight of polypropylene, 27 parts by weight of the Diels-Adler diadduct of hexachlorocyclopentadiene, 1,5-cyclooctadiene, 13 parts by weight of antimony trioxide, 6–10 parts of titanium dioxide and about 4 parts of disazodiacarbonamide.

EXAMPLE 8

Example 2 is repeated using a flexible polyurethane foam having a density of two pounds per cubic foot and a thermal conductivity of 0.3 Btu/sq. ft./hr. degrees F./inch as measured by ASTM D2326.

EXAMPLE 9

Example 2 is repeated using a high resilience polyurethane foam having a density of 2.7 pounds per cubic foot and a flame resistance characteristic of SE (self-extinguishing) as measured by ASTM D1692.

EXAMPLE 10

Example 2 is repeated using a flexible polyurethane foam as prepared in Example 4 of U.S. Pat. No. 3,391,092, the disclosure of which is incorporated herein by reference.

The thermocooling characteristics of the various components of the orthopedic device when heated to high temperatures, for example, about 300° F. are illustrated in the following time-temperature profile of a flat (blank) about 6½"×6½". The central platic member was about 69 mils thick. The insulating fabric was the aforedescribed Collins & Aikman no-burn fabric (7 oz. weight) about 15–18 mils thick. The other fabric was a knit (tricot) stabilized nylon and polyester blend about 12 mils thick. Both of the fabrics were applied to the plastic member by spreading an adhesive on one side of the plastic member and then applying the fabric and applying a heated iron to heat the fabric and adhesive to the temperature range to about 350°–380° F. The adhesive was spread to a thickness of about 3 mils. The insulating fabric was applied using the thermoplastic polyurethane adhesive described hereinbefore. The tricot adhesive was the thermosetting polyurethane described hereinbefore containing about 4% of the crosslinking diisocyanate.

The thermal properties were determined by first heating the device and then allowing it to cool in air (room temperature 69°–71° F.) and measuring the rates thereof. The device was positioned with the tricot fabric face about ⅜ of an inch away from the hot plate and parallel thereto. The hot plate was measured to have a surface temperature of about 409° F. The device was heated to the temperatures noted in the following table and then permitted to cool. A thermocouple $T_3$ was positioned on the central plastic member face which is bonded to the tricot and a thermocouple $T_4$ was on the side of the plastic member which is bonded to the insulating fabric. The time-temperature profile follows:

|  | Time (minutes) | Temperature °F. $T_4$ | Temperature °F. $T_3$ |
|---|---|---|---|
| Heating | 0 | 82 | 82 |
|  | 10 | 192 | 209 |
|  | 17 | 224 | 234 |
| Heat Source Removed | 21.5 | 268 | 323 |
| Cooling | 0.5 | 263 | 284 |
|  | 1.0 | 252 | 267 |
|  | 1.5 | 242 | 251 |
|  | 2.0 | 227 | 237 |
|  | 2.5 | 219 | 225 |
|  | 3.0 | 206 | 213 |
|  | 3.5 | 195 | 201 |
|  | 4.0 | 186 | 192 |
|  | 4.5 | 177 | 182 |
|  | 5.0 | 168 | 173 |
|  | 5.5 | 161 | 166 |
|  | 5.8 | 157 | 161 |
|  | 8.0 | 131 | 134 |
|  | 10.0 | 115 | 118 |
|  | 11.5 | 106 | 108 |

Physical manipulation of the device established that the forming period ended, i.e., the plastic had solidified, when the plastic temperature was about 130° F. In some cases this appeared closer to 129° F. which is within the range of accuracy of measurement. The same device was reheated several times and each time it solidifies at about 130° F. Other samples softened at somewhat lower temperatures, e.g., 124° F.–127° F.

This data is cnsistent with the developmental experience that the same device may be completely or partially reformed. and even reshaped, in whole or in part, many times. This provides means for correcting "fitting" errors, and also means for adjusting the shape of the device during its service life. It also provides the possibility of reusing the device which is particularly important in the poorer countries. Orthopedic devices having the insulated foam layer in place of the fabric layer provide even more forming time with at least as much protection to the patient.

The aforesaid time-temperature profile establishes that there was more than eight minutes of shaping and forming time, i.e., the time starting with the removal of the heat source, until solidification occurs. Practical testing of numerous samples having the nylon-polyester fabric on one side and the no-burn Collins & Aikman insulating fabric on the other side has established that when the device has been heated to over 300° F. and preferably to 325° F., there is at least 7½ minutes of shaping and forming time. Tests with other experimental devices in which the other fabric is not nylon-polyester, for example, cotton, have established that the cooling time to solidification may be different and in some cases appreciably shorter, for example, as little as 4½ minutes.

The actual cooling time for a given device may vary with the overall thickness and other dimensions of the device as well as the amount of heating time and ultimate temperature and and the cooling conditions. The devices having the insulating plastic foam layer, particularly thick layers, e.g., 125–250 mils thick, cooled more slowly and provided a larger temperature differential, e.g., at least 55°–60° F., between the outside of the foam layer, and the plastic sheet member.

Temperature determinations were also made on the outside of the insulated fabric layer during the time-temperature profile, and during other heating and cooling tests. It was found that when using the aforesaid 7 oz. Collins & Aikman no-burn fabric, the temperature differential between the outside of the fabric and the plastic was about 40° F. The temperature measurements sometimes indicated a variation of ±10° F., but were usually within ±5° F.

When the "blank" orthopedic device is severly shaped at temperatures above about 325° F., e.g., some portions bent around one axis and other portions bent around a perpendicular or other intersecting axis, there may be some displacement of plastic within the outer layers so that the resultant shaped (and usually formed) device may no longer be of a consistent uniform thickness.

Some practitioners who apply the orthopedic devices may wish to outline the shape, particularly when the shape is relatively intricate, in a pattern on the blank (flat) orthopedic device before cutting it into the rough shape and forming. This may be accomplished in several methods depending upon the fabrics involved. Certain fabrics, e.g., the woven blend of Kynol and Nomex described hereinbefore, may be marked with a marker, e.g., pen, pencil, crayon, etc. Alternately, a paper layer may be affixed to one of the surface layers by a pressure-sensitive adhesive. The surface of the paper may be marked and used as a pattern and the orthopedic device cut and shaped. The paper may be removed immediately after cutting or in some cases desirably retained until rough shaping is completed. It would then be stripped from the outer layer.

The orthopedic devices of the present invention have many advantages. When used as a relatively large support without severe bending, such as a back support, the orthopedic device supplies resilient support. When used as a cast it will immobilize. When used to keep a body part in bent position such as a knee cage, restraint in only one direction is required. The orthopedic devices have special utility for service where adjustment in the shape of the device is desirable during a protracted period of time. Thus, as the patient responds to treatment, change in position may be desirable. In the past with plaster casts, the old cast had to be removed and a new cast formed. The orthopedic devices of the present invention may be partially reshaped even when attached to the body by localized application of heat and molding.

One of the most important uses of orthopedic devices is support of the lumbo-sacral region of the back. Immobilization of the lower body area risks a number of ill effects including shrinkage of tendons, and elasticity loss and weakening of muscles. The orthopedic devices of the present invention provide effective support and permit stabilization and immobilization of the lower spine without the foregoing adverse effects. This results from the unique combination of physical properties which provide substantial immobilization by those portions of the device which are highly contoured and at the same time provide resilient support by other less contoured portions of the back support and thereby permit body movement. Because of the ability to be formed and molded directly upon the patient, it is possible to provide back supports (which have been impossible or very difficult to make using prior materials) which cover relatively diverse and/or large portions of the back and, in some cases, may overlap around the sides of the body or over the shoulder.

The orthopedic devices may be used in the veterinary field in a manner parallel to their use with humans.

The orthopedic devices may be placed in a pocket or pouch of a garment which encircles a part of the body and thereby positions the orthopedic device. For many applications it will be desirable that the orthopedic device should be placed directly against the body portion and encircle it, and therefore it is self attaching. For other applications, the orthopedic device should have loops or other means of attachment for belts and other types of bindings such as Velcro fasteners, etc. These may be affixed to or even incorporated into one or both of the fabric layers. In such instances they will be affixed to the fabric layer which is on the side of the orthopedic device away from the patient's skin, i.e., in most instances the outside fabric layer. Orthopedic devices may be formed in self-closing and fastening configurations or may be fastened in any and all ways known in the art today.

The orthopedic devices may be provided as flat blanks for molding and shaping by the ultimate user. They may also be provided in preformed shapes, such as a series of preformed back supports which will generally conform to the body portions of the appropriate size. These orthopedic devices would have the advantage over other preformed devices in that final adjustment to individual variations may be made. They will also have the advantages over prior orthopedic devices in their combination of rigidity and resilience in different directions.

The orthopedic devices are also useful when utilized to position the body (or a portion thereof) by accurately for radiation treatment.

The orthopedic devices having a foam outer surface may be used as per se, or as part of another orthopedic device to cushion or otherwise protect a portion (usually a boney portion) of the body.

Although the orthopedic devices will generally be conformed to the shape of the body, they may sometimes be shaped differently so as to make the body conform to the shape of the orthopedic device during service, e.g., a correctly formed arch support for use by a person having a fallen arch.

The discussion hereinbefore is primarily in connection with orthopedic devices which will be attached to the body. They may also be used in equipment which is not attached to the body but comes into contact with the body such as the seat of a chair, particularly an orthopedic chair, foot supports such as arch supports, and other portions of shoes and boots. They may be used in ski boots wherein relative rigidity in certain directions is desired in combination with resiliance in other directions of movement.

What is claimed is:

1. A shaped body consisting of a plastic sheet member of a thickness of 50 to 120 mils, a flexural strength of 3,000 to 14,000 psi, a flexural modulus of $0.5 \times 10^5$ to $7 \times 10^5$ psi and a Vicat softening point of 60° C. to 80° C., an insulating layer having a thickness of at least 10 mils and a coefficient of heat transfer below 2 cal/sec/cm$^2$/°C.$\times 10^{-4}$ on one side of said sheet member, and a protective layer on the other side of said sheet member, said sheet being shapeable to its final contours by heating to a temperature of 120° F. to 400° F. at said protective layer.

2. The shaped body defined in claim 1 wherein said protective layer is fabric bonded to the plastic sheet member and having a thickness between about 4 to 22 mils.

3. The shaped body defined in claim 1 wherein said insulating layer is a fabric layer.

4. The shaped body defined in claim 3 wherein said insulating layer is bonded to said sheet member with a thermoplastic adhesive.

5. The shaped body defined in claim 4 wherein said fabric is impregnated with said adhesive.

6. The shaped body defined in claim 1 wherein said insulating layer is a plastic foam layer.

* * * * *